United States Patent [19]

Melendez et al.

[11] Patent Number: 4,759,353

[45] Date of Patent: Jul. 26, 1988

[54] UNIVERSAL FOREARM SLING AND HUMERAL STABILIZER

[76] Inventors: Michael G. Melendez; Kathryn M. Melendez, both of 1300 Birch Banks, Sagle, Id. 83860

[21] Appl. No.: 9,931

[22] Filed: Feb. 2, 1987

[51] Int. Cl.$^4$ .............................................. A61F 5/40
[52] U.S. Cl. .......................................... 128/94; 128/77
[58] Field of Search ............... 128/94, 87 R, 83, 77, 128/89 R; 383/72

[56] References Cited

U.S. PATENT DOCUMENTS

| | | | |
|---|---|---|---|
| 209,723 | 11/1878 | Stowell | 383/72 |
| 2,306,715 | 12/1942 | Rubinstein | 128/94 |
| 4,209,011 | 6/1980 | Peck et al. | 128/87 R |
| 4,214,579 | 7/1980 | Ford | 128/77 X |
| 4,355,635 | 10/1982 | Bihl et al. | 128/94 |
| 4,372,301 | 2/1983 | Hubbard et al. | 128/94 |
| 4,510,928 | 4/1985 | Ackley | 128/94 |
| 4,572,172 | 2/1986 | Williams | 128/94 |
| 4,598,702 | 7/1986 | Lilla | 128/94 |
| 4,622,961 | 11/1986 | Christenson | 128/94 |
| 4,625,719 | 12/1986 | Chambers | 128/94 |
| 4,691,917 | 9/1987 | Battista | 128/94 X |

Primary Examiner—Robert A. Hafer
Assistant Examiner—Kevin G. Rooney
Attorney, Agent, or Firm—M. Reid Russell

[57] ABSTRACT

The present invention is in a universal forearm sling and humeral stabilizer that consists of a sling sack that is open along a top edge and at a wrist end and is formed of outer and inner layers, the outer layer consisting of a thin fabric material that can be water repellant, and can include pockets formed therein, and the inner layer formed of a suitable material for protecting from the elements a patient's forearm supported therein. The undersurface of the sling sack is supported from end to end by a strap secured longitudinally thereto. The strap bisects the sling sack and extends from the closed sling sack end to become a shoulder strap that ends in a swivel. The swivel is to couple to a ring whereto the ends of a lateral strap are secured, which lateral strap encircles the sling sack, proximate to the open end. The sling sack closed end is angled at the preferred angle of seventy five degrees (75°) from the horizontal to correspond to the correct anatomic axis for supporting the patient's humerus and elbow. Additionally, the sling sack provides points of attachment for ends of a waist strap or band that is for maintaining the sling to the patient's body. Further, the invention preferably includes a pouch for receiving the folded sling therein that will double as a glove for encasing the hand of the patient's injured arm.

15 Claims, 2 Drawing Sheets

UNIVERSAL FOREARM SLING AND HUMERAL STABILIZER

BACKGROUND OF THE INVENTION

1. Field of the Invention

This invention relates to sling devices for immobilizing a body member and particularly to a forearm-type sling for use with either injured arm to support and immobilize that arm and shoulder.

2. Prior Art

Supporting and immobilizing slings are, of course, well known. The traditional forearm sling is a square or rectangular section of cloth that is folded to support the injured member with the ends pulled around the patient's neck and tied into a knot. So arranged, the sling is suspended from a patient's neck area cradling and supporting an injured member. Additionally, a belt or the like could be fitted across the sling above the injured arm and secured around the patient's body for holding that injured arm against the patient's body. In recent years, a cloth sack-type sling has come into common use for performing the same function as this earlier tied sling. Such sack sling generally has an elongate shape and is open along a top edge and at the one end to receive the patient's forearm resting therein. The sack sling includes a strap that is secured at its ends to the sack proximate to the ends thereof, that strap to pass across the patient's shoulders and around their neck. This sack sling may include a tie or belt for supporting it to the patient's body. Such sack-type slings are more convenient than the earlier cloth tied slings, and provide essentially the same support. Prior to the present invention, no sling has been commercially available that provides both longitudinal support to the injured forearm along its length and for maintaining the sling to the patient's body, immobilizing the humerus. Heretofore, a separate wrap for stiffening the forearm or a casting of that forearm has been required to prohibit the forearm from sagging and, with certain types of injuries, both a sling and a separate humeral stabilizing arrangement have been required.

The present invention is an improvement over such earlier sack-type slings in that it is configured to support with a longitudinal strap an injured forearm along its entire length, is sloped at an optimum angle at its closed end to accommodate the patient's elbow and humerus, and includes a lateral wrist supporting strap that encircles the open end. The logitudinal strap provides essentially a continuous strap that extends the length of and along the closed end of the sling sack, continues across the patient's shoulders, and terminates in a swivel coupling that is for joining to a ring mounted to the ends of the lateral strap. Further, unlike earlier slings that incorporate a thin cloth-type strap for supporting the sling sack across the patient's neck, the sling strap of the present invention is preferably a web belting arrangement and, with the swivel coupling on the one strap end, the strap can be pivoted allowing the sling to be conveniently used for supporting either patient's arm. The swivel and ring coupling is easily detachable, facilitating installing the sling sack of the invention to cradle a patient's arm. Further, unlike earlier separate belts and like humeral supporting arrangements that have beem employed to maintain a sling to a patient's body, the present invention provides a waist strap arrangement whose length is adjustable and involves a belt with coupling ends. Each such coupling end is releasably attached to one of a pair of metal or fabric rings that are secured at intervals to the underside of the sling, for maintaining the sling in snug engagement to the body.

Additionally, where earlier slings have generally been made of a lightweight non-insulative material, the present invention forms the sling sack of an inner layer that is preferably a fleece or cotton and an outer layer that is preferably a slick material, which outer layer may be waterproof and may also include pockets formed in the opposite faces thereof for carrying personal items. Earlier slings, of course, have not involved such materials or features and, additionally, unlike earlier slings, the present invention includes a separate sack or pouch for containing the folded sling, which pouch can double as a glove. The present invention therefore provides a sling system for both maintaining the patient's injured arm supported from their neck and immobilized to their body, and for keeping that patient's arm and hand comfortable.

BRIEF SUMMARY OF THE INVENTION

It is therefore a principal object of the present invention to provide a universal sling for both supporting and immobilizing a patient's injured arm to their body, the sling to support the patient's forearm along its entire length.

Its another object of the present invention to provide a universal sling that includes a continuous strapping to longitudinally support the patient's forearm and their wrist, which sling can be utilized for supporting either arm, is adjustable for use with children or adults and includes a waist supporting strap arrangement.

Another object of the present invention is to provide a sling sack having a closed end that is sloped to an optimum angle that corresponds to the correct anatomic angle for supporting the humerus and elbow of a patient's damaged arm, the sling sack to be manufactured from two layers of material to provide both an attractive outer apperance and an inner lining.

Still another object of the present invention is to provide a universal sling that incorporates pocketing arrangements in the opposite sling faces, between inner and outer layers, the outer layer manufactured from a section of a lightweight and attractive material.

Still another object of the present invention is to provide, for carrying the universal sling, a pouch that receives the folded sling that will also accommodate a person's hand fitted therein and includes a drawstring arrangement for closing the pouch open end around the patient's wrist for use as a glove over the hand of their injured arm.

In accordance with the above objects, the present invention in a universal forearm sling and humeral stabilizer is constructed to be used to both support and provide orthopedic immobilization to a patient's damaged arm. The sling includes a sack that is open along the top and at one end to accommodate the patient's injured arm fitted therein. The other sack end is closed and is sloped at an optimal angle that corresponds to the correct anatomic angle for accommodating and supporting the patient's humerus from their elbow to their shoulder. The invention provides a strap that extends from the sack open end, longitudinally along the sack bottom and up the sloped end to project therefrom, the sling strap arranged to be passed around the patient's neck and terminates in a swivel connector end. A lateral strap is secured around the sack open end, the ends thereof terminating in a ring connector whereto the swivel connector is coupled, supporting the patient's forearm from their wrist to elbow, with the lateral strap supporting their wrist. The longitudinal strap is preferably continuous from the open sack end to terminate in the swivel connector. The longitudinal strap length is adjustable, with the strap to be threaded through a conventional buckle for increasing or decreasing the strap length so as to accommodate different sizes of patient's.

Spaced apart metal or cloth rings are preferably secured at intervals to the undersurface of the longitudinal strap, along the sack bottom for receiving coupling ends of a belly or waist strap that is fitted around the patient's midsection. The waist strap is preferably adjustable to accommodate its being fitted in an encircling arrangement around any size of patient's waist, immobilizing the patient's forearm against their torso.

Additional to the described sling with strapping and the waist strap, the present invention includes a pouch for maintaining the folded sling including the strapping therein. This pouch is preferably formed of a heat retaining material to be used also as a glove for receiving the patient's hand therein and includes an elastic or string-type drawstring arrangement for drawing and maintaining the sack pouch open end drawn around the patient's wrist.

Preferably, the sack portion of the sling of the present invention is formed of an inner layer of a fleece-type of material that, for cold weather use, is heat retaining for keeping the patient's injured arm warm, and may be of a thin material where the sling is to be used in warm weather. The sling sack preferably incorporates an outer layer that can be waterproof and colored to provide an attractive appearance. The outer layer is preferably formed to include pockets backed by the inner layer, which pockets are included on both sides of the sling and can be individually closed, preferably by Velcro ® type fasteners.

DESCRIPTION OF THE DRAWINGS

In the drawings is illustrated that which is presently regarded as the best mode for carrying out the invention.

DETAILED DESCRIPTION

Figure 1:
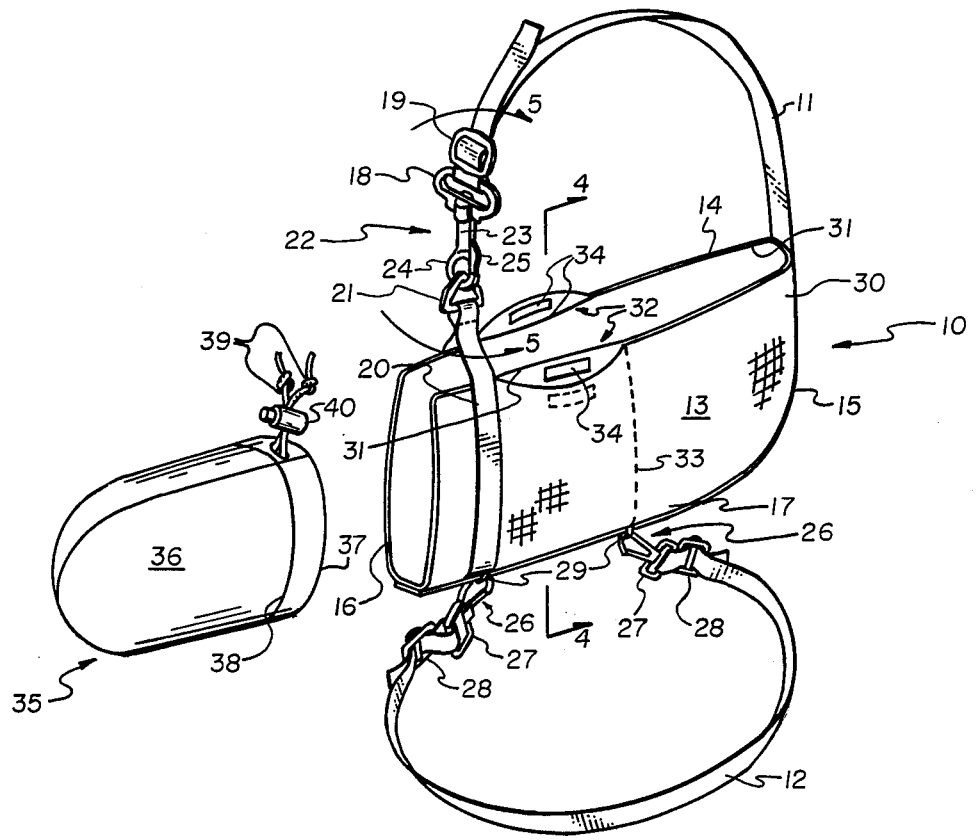
FIG. 1 is a perspective view of the universal forearm sling and humeral stabilizer of the present invention that includes a sack for receiving a patient's arm that is open along the top and at one end, showing pockets formed in the outer sack surface that have both been pulled outwardly and includes longitudinal and lateral strapping with a waist strap, which sling is shown aligned with a pouch for receiving the folded sling therein.

FIG. 1 shows a preferred embodiment of the present invention in a universal forearm sling and humeral stabilizer 10, hereinafter referred to as sling. The sling 10 is shown as including a sling sack 13 that is open across a top longitudinal edge 14 and at a wrist end 16. The sling sack 15 includes a longitudinal strap 11 and waist strap 12 extending therefrom, the strapping and sling sack shown in FIG. 1 as they would appear supporting a patient's right arm.

Figure 4:
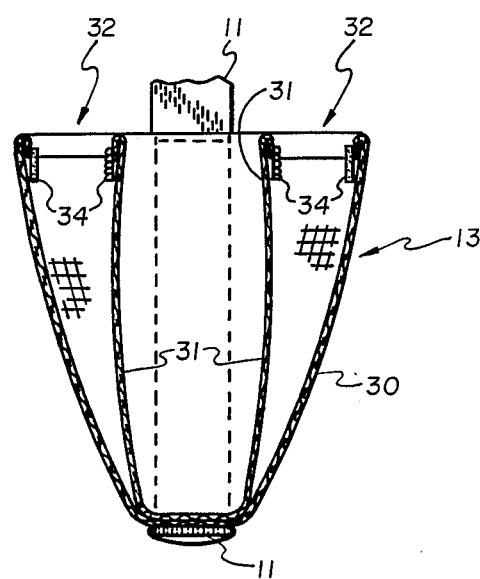
FIG. 4 is a vertical cross-sectional taken along the line 4—4 of FIG. 1 showing the sling sack as formed from outer and inner layers of material with the outer layer shown as having been formed into pockets that are closed with Velcro ® type fasteners.

Shown in FIGS. 1 and 4, the sling sack 13 open top edge 14 is to receive a patient's forearm fitted therethrough with their hand extending from the open end 16. The sling sack 13 is closed across an elbow end 15, which closed end is formed at an angle from the horizontal to optimumly accommodate a patient's humerus at the elbow, which angle corresponds to the patient's correct anatomic angle of approximately seventy five degrees (75°) to the horizontal, shown at A in FIG. 6.

Figure 2:
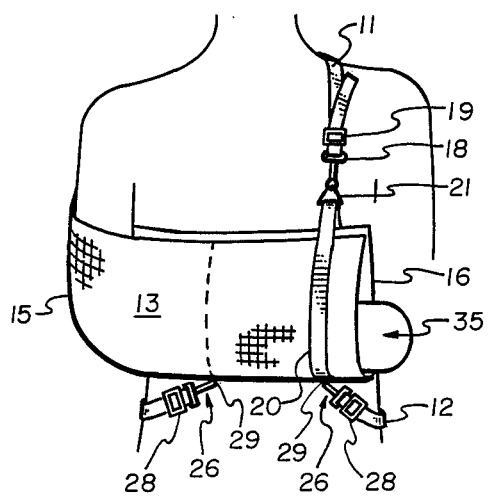
FIG. 2 shows the sling of FIG. 1 supporting a patient's right arm with the patient's hand maintained in the pouch.
Figure 3:
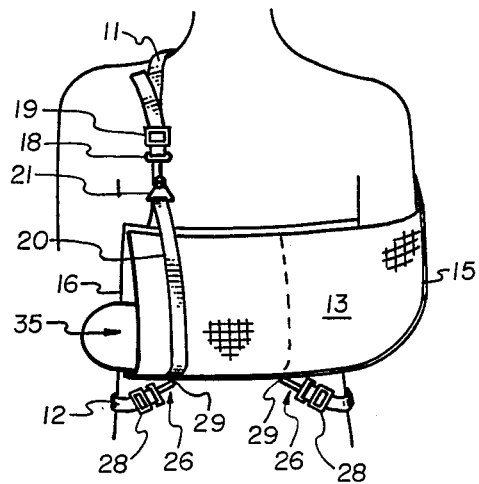
FIG. 3 shows the sling of FIG. 1 supporting a patient's left arm with the patient's hand maintained in the pouch.

FIGS. 2 and 3 show the sling 10 supporting, respectively, the forearm of a patient's right and left arms. So arranged, the sling will function as a universal sling in that it can be used to support either the right or left arm. Also, as the respective straps are adjustable in length, as set out below, the sling can be configured to accommodate a small or large patient. Shown best in FIGS. 1 and 6, the sling sack 13, along the lower longitudinal edge 17, includes the longitudinal strap 11 that is secured therealong, bisecting that sack from open end 16 to the top of closed end 15. The longitudinal strap 11 extends therefrom to become the sling strap, the end of which sling strap is fitted through a swivel eyelet 18 and thence back through a buckle 19. While the longitudinal strap 11 is preferably a continuous strap, it can be formed from sections that are joined together into the continuous strap 11. Longitudinal strap 11 is preferably a flexible web-type fabric belt with length adjustment thereof provided by appropriately threading the strap end through and back through buckle 19, thereby achieving a desired strap length.

Figure 5:
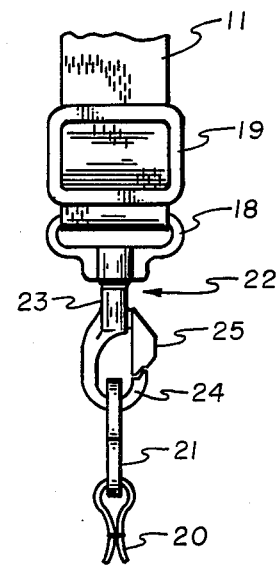
FIG. 5 is an exploded section taken within the line 5—5 of FIG. 1 showing a swivel connector mounted to the one end of the shoulder strap coupled to a ring that is secured to the lateral strap ends.
Figure 6:
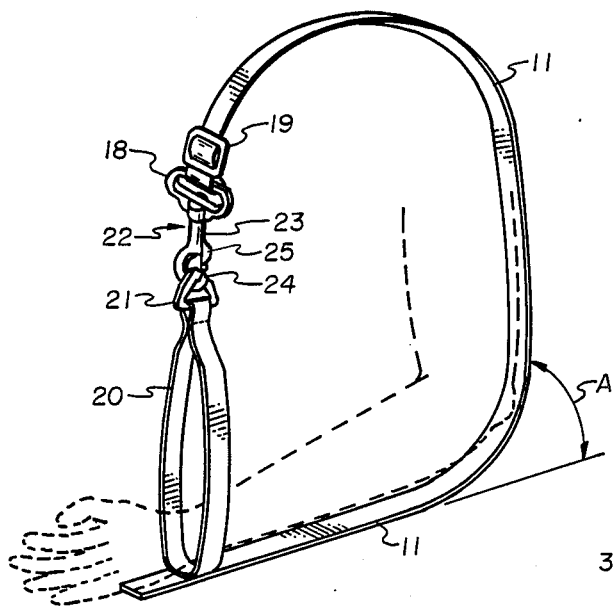
FIG. 6 shows the sling straps alone with a patient's arm shown in broken lines.

Shown in FIG. 6, the longitudinal strap 11 supports the patient's forearm along its entire length. Additional support is provided by a lateral strap 20 that is secured to encircle the sling sack 13 proximate to and just back from the open end 16 thereof. The lateral strap 20, as shown in FIG. 6, supports the patient's wrist, and the strap ends are secured through the lower ring of a ring connector 21. Ring connector 21, as shown best in FIGS. 1, 5, and 6, includes the lower ring and an upper ring for releasable connection to a swivel 22. Swivel 22, in turn, consists of the described swivel eyelet 18, wherefrom the end of a shaft 23 is pivotally connected to extend at a normal angle from the base of that swivel eyelet 18. The swivel shaft 23 opposite end terminates in a hook 24. The hook 24, across an opening thereof, includes a trigger 25 that is fitted into a track formed in the shaft side of the hook, the trigger to slide under the urgings of a spring biasing, not shown, to extend across that hook opening. Alternatively, the trigger 24 can be pivotally connected to one side of the hook opening to pivot across that hook opening, not shown. As shown in FIGS. 1, 5 and 6, the trigger 25 is urged against the spring biasing to retract across the hook opening to allow passage of the upper ring of ring connector 21 therethrough. The spring to then back across the hook 24, the free trigger end slanted outwardly to fit and lock under the side of the hook opening when a pressure urging the trigger 25 to travel back across the hook opening is released.

Swivel 22 functions to allow the strap 11 end to be turned so as to position the sling sack 13 to either of the attitudes shown in FIGS. 2 and 3 for supporting either a patient's right or left arm. As set out above, the longitudinal and lateral straps 11 and 20, respectively, provide support for a patient's forearm along its entire length and at the wrist, which longitudinal strap 11 length can be adjusted by appropriately drawing the strap free end through and back through buckle 18. The sling can therefore be used on either arm and by any size patient, functioning as a universal sling.

Shown best in FIG. 1, the sling 10 also preferably includes a waist strap or band 12 that is for maintaining the sling 10 to the patient's body. The waist strap or band for providing length adjustment to accommodate a range of waist sizes of patients has its ends threaded first through buckles 28 and thence through eyelet bases 27 of hooks 26 whereafter the waist strap ends are passed back through buckles 28. As shown in FIGS. 1, 2, and 3, the hooks 26 are individually fitted through one of a pair of rings or cloth strips 29 that are secured at intervals at their ends to be open thereacross and extend downwardly from the undersurface of the longitudinal strap 11. One strip 29 is preferably secured at the junction of the lateral strap 20 with the longitudinal strap 11. The other strip 29 is spaced therefrom along longitudinal strap 11. With the waist strap or band 12 length appropriately adjusted to a patient's waist and the hooks 26 coupled through strips 29, the waist strap or band 12 will then hold the sling sack 13 to the patient's body, as shown in FIGS. 2 and 3.

Shown in the sectional view of FIG. 4, the sling sack 13 is preferably formed of an outer layer 30 and an inner layer 31. The outer layer 30 can be a canvas-like material and is preferably a cotton polyester or a nylon that may be water repellant and can be colored appropriately to provide a pleasing and attractive appearance. The outer layer 30, as shown best in FIGS. 1 and 4, is preferably sewn laterally to the inner layer 31, shown at 33, to form identical pockets 32 in both sling sack 13 faces. The pockets 32 are open across their top ends and preferably are arranged to be closed utilizing closure arrangements such as Velcro ® strips 34. By having pockets 32 on both sling sack outer surface the patient is provided with a usable pocket on the outer sling sack surfaces, regardless of whether the sling 10 is being worn on their right or left arm, as illustrated in FIGS. 2 and 3. Each pocket 32 can be closed by pressing the strips of Velcro ® 34 together.

Figure 7:
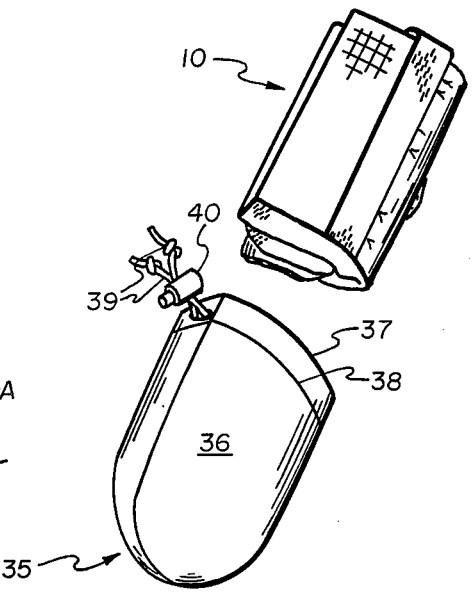
FIG. 7 shows the sling of the present invention folded and aligned for fitting into the open end of the pouch of FIG. 1.

For a sling 10 that is suitable for wear during cold weather, the sling sack 13 inner layer 31 is preferably formed of an acrylic fleece, wool, or like heat retaining material. Alternatively, where the sling 10 is to be used in warm weather, both the inner and outer layers 31 and 30 can be formed of a cotton polyester or like material material that will discourage heat retention. Shown in FIGS. 1 and 7, the sling 10 also preferably includes a separate pouch 35 that is dimensioned to accommodate the sling 10 folded and fitted therein for storage and transport. The pouch 35 is preferably formed from a section of acrylic fleece, wool or like insulating material 36 that is folded on itself and is sewn so as to leave one end 37 open. The pouch open end 37 is preferably also folded upon itself and is sewn appropriately, as illustrated at 38, to form a continuous pocket around that open end, which pocket is for receiving an elastic or string-type drawstring 39 threaded therethrough. Which drawstring 39 ends are to receive a slide 40 fitted thereon. The drawstring 39 is pulled through slide 40 to shorten the drawstring length within the pouch pocket 38. The pouch open end can be opened or closed so as to accommodate the sling 10 after it has been folded, being fitted and the pouch open end. Whereafter, the pouch open end 37 can be closed by pulling that drawstring through the slide. This arrangement also allows the pouch 35 open end 37 to be closed around a patient's wrist and worn as a glove, as illustrated in FIGS. 2 and 3.

The sling 10 of the present invention, as shown in FIGS. 1 through 7, is universal in that it can be used is for supporting either patient's arm, the strap 11 being pivotal at swivel 22, and the length of strap 11 is adjustable at buckle 19 for wear by any size of patient. The sling sack 13 is preferably angled at the elbow to an angle of seventy five degrees (75°) to the horizontal that corresponds to the correct anatomic angle for supporting that arm such that the patient's humerus will be properly aligned with their shoulder joint for comfortable support. The longitudinal strap 11 provides support for the forearm along its entire length, prohibiting a sagging thereof, with the patient's wrist supported by the lateral strap 20. The respective longitudinal and lateral strapping provides for both supporting the injured arm and limiting sagging thereof. With the sling sack 13 and strapping 11 and 20 supporting the patient's forearm, a waist band or belt 12 functions as a humeral stabilizer, maintaining the sling sack containing the patient's arm against their body. Finally, the sling 10 is versatile in that it preferably incorporates, as the sling sack portion, an outer layer 30 wherein a pocket 32 is formed and an inner layer 31 that is formed of a material that is selected to keep the patient's forearm warm or cool depending upon the time of year the sling is intended for use in. The sling 10 is arranged to be folded so as to be contained in a pouch 35 that will double as a glove for covering the hand of the patient's injured arm.

Hereinabove is set out a preferred embodiment of the present invention in a universal forearm sling. It should, however, be understood that the present disclosure is made by way of example only and that variations or changes thereto are possible without departing from the subject matter coming within the scope of the accompanying claims, which claims we regard as our invention.

What is claimed is:

1. A universal forearm sling and humeral stabilizer comprising, a fabric sling sack formed from a section of material that is folded longitudinally upon itself having a fold length to contain a patient's forearm supported on that fold, said sling sack having opposite first and second ends, the first end open therealong to accommodate a patient's hand fitted therethrough, the second end closed and angled from the horizontal to approximate the angle from the horizontal that a patient's humerus will occupy when their forearm is supported in the sling sack, the second closed end snugly fitting against and supporting that upper arm; a longitudinal strap means that is a fabric belt and is secured to said sling sack along its folded edge from said first open end along said folded edge and said closed second end and extends from said closed second end as a sling strap means that is for fitting around the patient's neck; a lateral strap means that is secured to said sling sack, proximate to the open first end thereof, that terminates in a coupling means; and a strap end coupling means secured to the end of said sling strap means for releasable connection to said coupling means.

2. A universal forearm sling and humeral stabilizer as recited in claim 1, further including means for maintaining said sling sack against the patient's body.

3. A universal forearm sling and humeral stabilizer as recited in claim 2, wherein the means for maintaining said sling sack against the patient's body consists of a first waist band connecting strip means that is secured at its ends at the junction of the longitudinal strap means and the lateral strap means to be open therethrough and a second waist band connecting strip means that is also secured at its ends to said longitudinal strap, to be open therethrough and spaced apart from said first waist band connecting strip means.

4. A universal forearm sling and humeral stabilizer as recited in claim 3, wherein the waist strap or band includes hook means on the ends thereof each hook means for releasably coupling to one of the first and second waist band connecting strip means; and the waist strap or band includes at least one buckle means to receive the waist strap or band ends therethrough for adjusting the length thereof.

5. A universal forearm sling and humeral stabilizer as recited in claim 1, wherein the fabric sling sack is formed from a section of overlaid inner and outer layers, said outer layer formed from a section of lightweight material.

6. A universal forearm sling and humeral stabilizer as recited in claim 5, wherein the outer layer is formed from a water repellent material.

7. A universal forearm sling and humeral stabilizer as recited in claim 5, wherein the outer layer is secured to the inner layer so as to form open pockets in the opposite sling sack faces; and closure means for closing said pockets.

8. A universal forearm sling and humeral stabilizer as recited in claim 5, wherein the inner layer is a section of a fleece-type of heat retaining material.

9. A universal forearm sling and humeral stabilizer as recited in claim 5, wherein the inner and outer layers are each formed of sections of a lightweight material.

10. A universal forearm sling and humeral stabilizer as recited in claim 9, wherein the inner and outer layers are each a cotton polyester.

11. a universal forearm sling and humeral stabilizer as recited in claim 1, wherein the longitudinal and lateral strap means are each web-type fabric belts, the longitudinal strap means secured to the sling sack longitudinal fold from the edge of the first end and across the second closed end, the lateral strap means secured around the sling sack, proximate to the open first end thereof.

12. A universal forearm sling and humeral stabilizer as recited in claim 1, wherein the end of the sling strap means that is the extension of the longitudinal strap means is fitted through a buckle and through said strap end coupling means and is then threaded back through said buckle for providing length adjustment thereto; and said sling strap means end coupling means is a swivel that consists of a ring base wherethrough the sling strap means end is fitted, a shaft that is pivotally coupled to extend from said ring base and a hook end formed in the shaft end opposite to said ring base with, said hook end including an opening for receiving the coupling means fitted therethrough.

13. A universal sling and humeral stabilizer as recited in claim 12, wherein a trigger means consisting of a flexible bar that is coupled on its one end to one side of the hook end said trigger means flexible bar extending across the hook opening; and the coupling means are first and second rings, the first ring formed as the end of the lateral strap means that receives the second ring fitted through said second ring to pass through said hook end opening to be maintained within said hook end opening by said trigger means.

14. A universal sling and humeral stabilizer as recited in claim 1, wherein the second sling sack closed end is angled approximately seventy five degrees (75°) from the horizontal.

15. A universal sling and humeral stabilizer as recited in claim 1, further including a pouch formed of an insulative fabric material that is open at one end and includes a drawstring means at said pouch open end for drawing together the material of said pouch open end so as to reduce the circumference of said pouch open end.

* * * * *